US010604801B2

(12) United States Patent
Albitar (10) Patent No.: US 10,604,801 B2
(45) Date of Patent: Mar. 31, 2020

(54) DEEP SEQUECING OF PERIPHERAL BLOOD PLASMA DNA AS A RELIABLE TEST FOR CONFIRMING THE DIAGNOSIS OF MYELODYSPLASTIC SYNDROME

(71) Applicant: NeoGenomics Laboratories, Inc., Fort Myers, FL (US)

(72) Inventor: Maher Albitar, Valley Center, CA (US)

(73) Assignee: NEOGENOMICS LABORATORIES, INC., Fort Myers, FL (US)

( * ) Notice: Subject to any disclaimer, the term of this patent is extended or adjusted under 35 U.S.C. 154(b) by 547 days.

(21) Appl. No.: 14/937,937

(22) Filed: Nov. 11, 2015

(65) Prior Publication Data

US 2016/0130648 A1    May 12, 2016

Related U.S. Application Data

(60) Provisional application No. 62/083,432, filed on Nov. 24, 2014, provisional application No. 62/078,921, filed on Nov. 12, 2014.

(51) Int. Cl.
*C12Q 1/68* (2018.01)
*C12Q 1/6874* (2018.01)
*C12Q 1/686* (2018.01)
*C12Q 1/6886* (2018.01)

(52) U.S. Cl.
CPC .......... *C12Q 1/6874* (2013.01); *C12Q 1/686* (2013.01); *C12Q 1/6886* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

2013/0059301 A1   3/2013   Gelsi-Boyer et al.

FOREIGN PATENT DOCUMENTS

| WO | 2011098901 A1 | 8/2011 | |
|---|---|---|---|
| WO | WO2012/174419 | * 12/2012 | ............... C12Q 1/68 |
| WO | WO2013/159035 | 10/2013 | |

OTHER PUBLICATIONS

Thangavelu (The American Society of Human Genetics, Oct. 19, 2014; poster abstract).*
Mussolin et al; Journal of Cancer, 2013, vol. 4, pp. 323-329.*
Elshimali et al; Int. J. Mol. Sci. 2013; vol. 14,pp. 18925-18958.*
Papaemmanuil et al; Bood, vol. 122, pp. 3616-3627.*
Ahmed, M., et al., Use of plasma DNA in detection of loss of heterozygosity in patients with multiple myeloma; European Journal of Haematology, Sep. 2003; 71(3): 174-178 (Abstract).

Albitar, M., et al., Myelodysplastic syndrome is not merely "preleukemia". Blood, Aug. 2002, 100(3): 791-798.
Albitar, M., (2004) Myelodysplastic syndrome: from morphology to biology; Current Hematology Reports, May 2004, 3(3): 159-164 (Abstract).
Bejar, R., et al., Clinical effect of point mutations in myelodysplastic syndromes. New England Journal of Medicine, 2011 364 (26): 2496-2506.
Bejar, R. et al., The importance of subclonal genetic events in MDS. Blood, 2013, 122 (22): 3550-3551.
Chen, K. et al., Clinical Actionability Enhanced through Deep Targeted Sequencing of Solid Tumors; Clinical Chemistry, 2015, 61(3): 544-553.
Giles F.J., et al., Plasma-based testing as a new paradigm for clinical testing in hematologic diseases. Expert Review of Molecular Diagnostics, Sep. 2007 7(5): 615-623 (Abstract).
Greenberg, P.L., Molecular and genetic features of myelodysplastic syndromes; International Journal of Laboratory Hematology; Jun. 2012; 34(3): 215-222 (Abstract).
Haferlach, T., et al., Landscape of genetic lesions in 944 patients with myelodysplastic syndromes. Leukemia, 2014, 28: 241-247.
Itzykson, R., et al., Somatic mutations and epigenetic abnormalities in myelodysplastic syndromes. Best Practice & Research Clinical Haematology, Dec. 2013; 26(4): 355-364 (Abstract).
Jilani I., et al., Better detection of FLT3 internal tandem duplication using peripheral blood plasma DNA. Leukemia, Jan. 2003, 17(1): 114-119 (Abstract).
Kerbauy, D.B., et al., Apoptosis and antiapoptotic mechanisms in the progression of myelodysplastic syndrome. Experimental Hematology, Nov. 2007; 35(11): 1739-1746.
Kitamura, T., et al., The molecular basis of myeloid malignancies. Proceedings of the Japan Academy. Series B, Physical and Biological Sciences, 2014; 90(10): 389-404.
Ma, W., et al., Plasma RNA as an alternative to cells for monitoring molecular response in patients with chronic myeloid leukemia. Haematologica, Feb. 2007; 92(2): 170-175.
Ma, W., et al., Higher detection rate of JAK2 mutation using plasma. Blood, Apr. 2008; 111(7): 3906-3907.
Ma, W., et al., Detection of nucleophosmin gene mutations in plasma from patients with acute myeloid leukemia: clinical significance and implications; Cancer Biomarkers, 2009; 5(1): 51-58, Abstract.
Malcovati, L., et al., Driver somatic mutations identify distinct disease entities within myeloid neoplasms with myelodysplasia. Blood, Aug. 2014; 124(9): 1513-1521.
Raza, A., et al. The genetic basis of phenotypic heterogeneity in myelodysplastic syndromes. Nature Reviews Cancer, Dec. 2012; 12(12): 849-859, Abstract.

(Continued)

*Primary Examiner* — Jehanne S Sitton
(74) *Attorney, Agent, or Firm* — Eleanor Musick; Musick Davison LLP (57) ABSTRACT

Methods are provided for treating, managing, diagnosing and monitoring myelodysplastic syndrome and other hematologic malignancies. These methods comprise the next generation sequencing analysis conducted on cell-free DNA from peripheral blood plasma or serum.

12 Claims, 2 Drawing Sheets

(56) References Cited

OTHER PUBLICATIONS

Rogers, A., et al., Relative increase in leukemia-specific DNA in peripheral blood plasma from patients with acute myeloid leukemia and myelodysplasia. Blood, Apr. 2004; 103(7): 2799-2801.

Steensma, D.P., Myelodysplastic Syndromes: Diagnosis and Treatment. Mayo Clinic Proceedings, Jul. 2015; 90(7): 969-983, Abstract.

Thol, F., et al., Frequency and prognostic impact of mutations in SRSF2, U2AF1, and ZRSR2 in patients with myelodysplastic syndromes. Blood, Apr. 2012; 119(15): 3578-3584.

Yeh, C.H., et al., Plasma-based detection of clonality in lymphoid malignancies. European Journal of Haematology, Jun. 2009; 82(6): 450-453.

Zeidan, A.M., et al., "Current therapy of myelodysplastic syndromes", Blood Rev. Sep. 2013; 27(5): 243-259).

Luthra, R., et al., "Next-generation sequencing-based multigene mutational screening for acute myeloid leukemia using MiSeq: applicability for diagnostics and disease monitoring", Haematologica, 2014; 99(3): 465-473.

Fernandez-Mercado, M., et al., "Targeted re-sequencing analysis of 25 genes commonly mutated in myeloid disorders in del(5q) myelodysplastic syndromes", Haematologica, 2013; 98(12): 1856-1864.

Mori, A., et al., "Next generation sequencing: new tools in immunology and hematology", Blood Res., Dec. 2013; 48(4): 242-249.

Albitar, F., et al. "Deep Sequencing of Peripheral Blood DNA as a Reliable Method for Confirming the Diagnosis of Early Myelodysplastic Syndrome", Blood, Dec. 2014; 124(21): 1909 (Abstract).

Thangavelu, M., et al. "Molecular profiling in diagnosis and determining prognosis of "early" myelodysplastic syndrome", Poster Abstract 3370S, Presented at the 64th Annual Meeting of The American Society of Human Genetics, Oct. 19, 2014.

Ma, W. et al., Proteasome Enzymatic Activities in Plasma as Risk Stratification of Patients with Acute Myeloid Leukemia and Advanced-Stage Myelodysplastic Syndrome, Clin Cancer Res, 2009; 15(11):3820-3826.

Cottrell, C.E., et al., Validation of a Next-Generation Sequencing Assay for Clinical Molecular Oncology; Journal of Molecular Diagnostics, Jan. 2014; 16(1): 89-105 (Epub Nov. 6, 2013).

Ma, W., et al., Plasma as a source of mRNA for determining IgV-H mutation status in patients with chronic lymphocytic leukaemia, British Journal of Haematology, Apr. 2006; 133: 690-692.

Bejar, R. et al. "O-024 Next generation sequencing of 213 MDS patient samples identifies mutations profiles associated with response to hypomethylating agents and overall survival", Leukemia Research, May 1, 2013, vol. 37, No. s19.

European Application 15858705.5, Extended European Search Report dated Mar. 9, 2018, 7 pages.

Itzykson, R. et al., "Prognostic score including gene mutations in chronic myelomonocytic leukemia", J. Clinical Oncology, Jul. 1, 2013, pp. 2428-2436, vol. 31.

\* cited by examiner

|       | 1  | 2  | 3 | 4  | 5 | 6  | 7  | 8 | 9  | 10 | 11 | 12 | 13 | 14 | 15 | 16 |
|-------|----|----|---|----|---|----|----|---|----|----|----|----|----|----|----|----|
| TET2  | 41 |    |   |    | 6 |    |    |   |    | 8  | 41 | 38 | 35 |    | 6  |    |
| CBL   | 29 |    |   | 45 |   |    |    |   | 73 |    |    |    |    | 35 |    |    |
| ASXL1 | 5  |    |   |    |   |    | 44 |   |    | 10 | 6  |    |    |    | 7  |    |
| U2AF1 | 32 |    |   |    | 6 |    |    |   |    | 9  | 18 |    |    |    |    |    |
| RUNX1 |    |    | 7 |    | 8 |    |    | 7 |    |    |    |    |    |    | 8  |    |
| IDH2  |    |    |   | 50 | 7 |    |    |   |    | 8  |    |    |    |    | 7  |    |
| SF3B1 |    |    |   |    | 5 | 38 |    |   |    | 19 | 10 |    |    |    |    |    |
| EZH2  |    |    |   |    | 7 |    |    |   | 41 |    | 7  |    |    |    | 7  |    |
| IDH1  |    | 50 |   |    |   |    |    |   |    | 13 |    |    |    |    |    | 19 |
| TP53  |    |    | 7 |    |   |    |    |   |    | 9  | 7  |    |    |    |    |    |
| ETV6  |    |    | 5 |    |   |    |    |   |    |    | 6  |    |    |    |    |    |
| ZRSR2 |    |    |   |    |   |    |    |   |    | 6  |    |    |    |    |    |    |

DEEP SEQUECING OF PERIPHERAL BLOOD PLASMA DNA AS A RELIABLE TEST FOR CONFIRMING THE DIAGNOSIS OF MYELODYSPLASTIC SYNDROME

CROSS-REFERENCE TO RELATED APPLICATIONS

This application claims the benefit of priority from U.S. Provisional Application 62/083,432, filed Nov. 24, 2014, and U.S. Provisional Application 62/078,921, filed Nov. 12, 2014, the entire disclosures of which are incorporated herein by reference.

TECHNICAL FIELD

This invention relates to compositions and methods for diagnosing, monitoring, treating and managing patients with myelodysplastic syndromes and other hematologic malignancies.

BACKGROUND OF THE INVENTION

Myelodysplastic syndromes (MDSs) are a heterogeneous group of clonal hematologic disorders characterized by ineffective hematopoiesis and dysplasia. In MDS, genomic abnormalities accumulate in a hematopoietic stem cell leading to peripheral cytopenias of varying degrees of severity, as a consequence of multilineage differentiation impairment, and, in the early phases, bone marrow (BM) apoptosis. Morbidity and mortality in the disease results from cytopenias or transformation to acute myeloid leukemia, which may both lead to serious infectious diseases, anemia or hemorrhage caused by dysfunction and reduction of blood cells.

Cytopenia (low blood cell count) results from a high rate of apoptosis within the bone marrow environment and consequent lack of release of cells into the peripheral blood circulation (Kitamura et al, 2014; Kerbauy et al, 2007). Diagnosing MDS can be challenging, especially during early stages when a patient's symptoms include cytopenia without an increase in blasts. There are numerous reactive processes that cause cytopenia including drug reaction, nutritional or hormonal deficiencies, and autoimmune diseases or chronic infection.

The major criteria for diagnosing MDS are the presence of peripheral cytopenia and dysplasia. However, evaluating dysplasia is subjective and can be difficult without bone marrow biopsy. Yet, proper and early diagnosis is very important for treating and managing progression of MDS because a chance for remission is much higher if MDS is detected prior to the stage where it has progressed to leukemia.

In patients presenting with cytopenia, MDS should be considered, but confirmation of diagnosis requires bone marrow biopsy and morphologic and cytogenetic evaluation. The diagnosis of MDS currently requires a multidisciplinary approach involving hematologic, morphologic and cytogenetic analyses, and may be difficult to render due to the fact that only about half of patients demonstrate cytogenetic abnormalities. The choice of therapies used to treat MDS heavily depends on disease severity and the risk of progression to more advanced disease. The ability to accurately formulate prognosis is therefore an essential component of patient care.

Current prognostic scoring systems consider karyotypic abnormalities and certain clinical features to stratify MDS patients into risk groups. Some karyotypic abnormalities help establish prognosis and can be associated with a specific clinical phenotype. However, more than half of MDS patients have a normal karyotype, and patients with identical chromosomal abnormalities remain clinically heterogeneous. It is extremely difficult to rely on subjective morphologic features to confirm the diagnosis of MDS, when the karyotype is normal and blasts are not increased.

Molecular evaluation can be helpful in providing objective means for the demonstration of abnormal mutant clone and confirmation of the diagnosis of MDS (Itzykson et al, 2013; Bejar et al, 2011; Haferlach et al, 2014; Thol et al, 2012; Malcovati et al, 2014). Due to the cytopenia in peripheral blood, molecular studies of DNA extracted from peripheral blood cells may not identify abnormal clones with adequate sensitivity; hence samples obtained from bone marrow are considered more reliable for detecting molecular abnormalities and confirming diagnosis of MDS.

The detected abnormalities have clinical implication on prognosis and determining therapy. In addition, it is important to test patients by using sensitive methods that are capable of detecting the presence of subclones that may dictate the overall prognosis (Bejar et al, 2013). MDS is a disease of excessive apoptosis in bone marrow, DNA resulting from this apoptosis is abundant in circulation because hematopoietic cells are immersed in blood; these cells pour their contents during apoptosis or necrosis through blood in the form of apoptotic bodies, exosomes, microvessels, or DNA-protein complexes (Giles et al, 2007).

There is a need for a reliable accurate method to diagnose MDS, especially at an early stage. Such methods will be helpful for identifying a patient who will benefit from a treatment for MDS. Further, as current methods rely on bone marrow biopsy which is a highly invasive and painful procedure, a significant advancement in treatment and diagnostics can be achieved with a procedure which does not require obtaining a sample from bone marrow.

SUMMARY OF THE INVENTION

In one embodiment, the invention provides a method of treating a patient for myelodysplastic syndrome (MDS), comprising a step of identifying the patient as an MDS patient by performing a mutation analysis comprising next generation sequencing (NGS) on cell-free DNA from patient's peripheral blood plasma or serum. This method can be performed without obtaining a bone marrow sample from the patient.

One embodiment provides a method of diagnosing and managing a patient. This method comprises a step of obtaining a cell-free DNA sample from peripheral blood plasma or serum of the patient; performing a mutation analysis of the cell-free DNA sample, wherein the mutation analysis comprises a procedure selected from the group consisting of: next-generation sequencing (NGS), polymerase chain reaction (PCR), hybrid capture and any combination thereof; and administering to the patient a treatment for management of a hematologic malignancy selected from the group consisting of myelodysplastic syndrome (MDS), leukemia, lymphoma and myeloma, if the mutation analysis detects a DNA mutation in the cell-free DNA sample.

One embodiment provides a method of diagnosing and managing a patient with MDS. This method comprises a step of obtaining a cell-free DNA sample from peripheral blood plasma or serum of the patient; performing a mutation analysis of the cell-free DNA sample, wherein the mutation analysis comprises a procedure selected from the group consisting of: next-generation sequencing (NGS), polymerase chain reaction (PCR), hybrid capture and any combination thereof; and administering to the patient a treatment for management of myelodysplastic syndrome (MDS), leukemia, lymphoma and myeloma, if the mutation analysis detects a DNA mutation in the cell-free DNA sample.

The method can aid in diagnosing and managing a patient at very early stages of disease, including a patient who has an increase in bone marrow blasts of less than 5% in comparison to a healthy control. The method is also suitable for patients who are presented with cytopenia, but do not manifest apparent karyotypic abnormalities.

In some embodiments, the mutation analysis is performed on MDS-associated genes, including such genes as ASXL1, ETV6, EZH2, IDH1, IDH2, NRAS, CBL, RUNX1, SF3B1, SRSF2, TET2, TP53, U2AF1, ZRSR2 and any combination of the genes. A treatment for MDS is administered to a patient whose cell-free DNA sample reveals a mutation in at least one of the following genes: ASXL1, ETV6, EZH2, IDH1, IDH2, NRAS, CBL, RUNX1, SF3B1, SRSF2, TET2, TP53, U2AF1, and ZRSR2. Various treatments can be used, including a growth factor, blood transfusion, desferoxamine, erythropoietin, a chemotherapeutic agent, stem cell transplant, and any combination thereof.

Further embodiments provide a method of management and monitoring for myelodysplastic syndrome (MDS). This method comprises at least the following steps: selecting a patient from a group of patients presented with cytopenia; obtaining a cell-free DNA sample from the patient's blood plasma or serum; conducting a mutation analysis on the cell-free DNA sample for MDS-associated genes; and administering a treatment for management of MDS to a patient whose cell-free DNA sample comprises one or more mutations in the MDS-associated genes. The MDS-associated genes may be selected form the group consisting of ASXL1, ETV6, EZH2, IDH1, IDH2, NRAS, CBL, RUNX1, SF3B1, SRSF2, TET2, TP53, U2AF1, ZRSR2 and any combination thereof.

In some embodiments, the step of obtaining a cell-free DNA sample from the patient's peripheral blood plasma and the step of conducting the mutation analysis on the cell-free DNA sample for the MDS-associated genes are repeated after the treatment has begun, and wherein the treatment is modified if additional mutations in the MDS-associated genes are detected.

Further embodiments provide a method of diagnosing and monitoring a hematologic malignancy selected from a group consisting of MDS, leukemia, lymphoma, myeloma and any combination thereof in a patient. This method comprises the following steps: extracting cell-free DNA from a peripheral blood plasma sample or serum of the patient; using next generation sequencing, conducting mutation analysis in a panel of MDS-associated genes in the cell-free DNA, wherein the detection of one or more mutations in one or more of the panel of MDS-associated genes is indicative of the presence of the hematologic malignancy; and determining a treatment protocol for the patient based on the detection of one or more mutations. In some embodiments for the method, the MDS-associated genes are selected from the group consisting of: ASXL1, ETV6, EZH2, IDH1, IDH2, NRAS, CBL, RUNX1, SF3B1, SRSF2, TET2, TP53, U2AF1, ZRSR2 and any combination thereof.

Further embodiments utilize deep sequencing of cell-free DNA from patient's peripheral blood plasma or serum to diagnose MDS.

A method is also provided for diagnosing and monitoring a patient for myelodysplastic syndrome (MDS) by analyzing cell-free DNA in peripheral blood plasma for mutations by using next generation sequencing (NGS).

DETAILED DESCRIPTION

The invention provides a method by which a patient can be diagnosed for myelodysplastic syndrome (MDS), including patients with MDS at very early stages. The test detects and analyzes cell-free DNA sample from peripheral blood plasma or serum by using next generation sequencing (NGS) and is performed without the need for obtaining bone marrow biopsy. In further embodiments, NGS can be used in combination with other sensitive tests such as PCR (Polymerase Chain Reaction) and hybrid capture. In further embodiments, at least one of the following tests can be used: NGS, PCR and hybrid capture.

The invention also provides a method by which a patient can be diagnosed for other hematologic malignancies such as leukemia, lymphoma and myeloma. The term "hematologic malignancy" is used interchangeably with the term "blood cancer." This method can diagnose a patient at very early stages. The test detects and analyzes cell-free DNA sample from peripheral blood plasma or serum by using next generation sequencing (NGS) and is performed without the need for obtaining bone marrow biopsy.

In further embodiments, NGS can be used in combination with other sensitive tests such as PCR (Polymerase Chain Reaction) and hybrid capture. In further embodiments, at least one of following tests can be used: NGS, PCR and hybrid capture.

Further embodiments provide a method of management or treatment for MDS and other hematologic malignancies, comprising a step of performing a mutation analysis of a cell-free DNA sample from peripheral blood plasma or serum. In this method, the mutation analysis comprises next generation sequencing (NGS) which in some embodiments can be performed in combination with PCR and hybrid capture.

A person of skill will appreciate that the term "treatment" is understood in this disclosure broadly and does not require a complete cure from MDS or other hematologic malignancies. The term "treatment" may be used interchangeably with the term "management." Any improvement in patient's condition or any stabilization of the patient's condition is considered to be treatment or management. In addition to stabilizing and/or improving, treatment or management also may include delaying, ameliorating or controlling progression of MDS or other hematologic malignancies, even if it does not result in putting the disease into remission.

In some embodiments, treatment or management may include administering to a patient diagnosed as a patient with MDS or with some other hematologic malignancy at least one therapeutic agent selected from growth factors, blood transfusions, desferoxamine, erythropoietin, chemotherapeutic agents and stem cell transplants. Suitable growth factors include, but are not limited to, granulocyte colony stimulating factor, granulocyte macrophage-colony stimulating factor, interleukin-11, and androgens. Suitable chemotherapeutic agents include, but are not limited to, cytarabine. Other suitable chemotherapeutic agents include, but are not limited to, idarubicin, topotecan and fludarabine. Suitable stem cells include, but are not limited to, blood-forming stem cells.

In one embodiment, the instant method comprises a screening for mutations in genes which associate with MDS and other hematologic malignancies. Such genes may include at least one of the following genes: ASXL1, ETV6, EZH2, IDH1, IDH2, NRAS, CBL, RUNX1, SF3B1, SRSF2, TET2, TP53, U2AF1, and ZRSR2. In some embodiments, other genes can be analyzed in addition to any of ASXL1, ETV6, EZH2, IDH1, IDH2, NRAS, CBL, RUNX1, SF3B1, SRSF2, TET2, TP53, U2AF1, and ZRSR2.

It will be appreciated that the term "MDS-associated genes" is understood broadly and includes any genes known to be mutated in patients with MDS, including such genes, mutations in which have been shown to correlate with an onset, progression and/or prognosis of MDS.

It will be appreciated that the term "blood cancer-associated genes" is understood broadly and includes any genes known to be mutated in patients with hematologic malignancies, including such genes, mutations in which have been shown to correlate with an onset, progression and/or prognosis of any blood cancer. Such genes include, but are not limited to ASXL1, ETV6, EZH2, IDH1, IDH2, NRAS, CBL, RUNX1, SF3B1, SRSF2, TET2, TP53, U2AF1, and ZRSR2.

It will be further appreciated that the term "early stages of MDS" is to be understood broadly and includes patients presented with cytopenia, but without a significant increase in bone marrow blasts detected. Such patients include those whose blast count is increased in comparison to a healthy control by less than 5%.

The term "mutation" is understood broadly and includes DNA point mutations, deletions, insertions and translocations. The term "mutation analysis" is to be understood broadly and includes identifying at least one of the following mutations in DNA: DNA point mutation, DNA deletion, DNA insertion and DNA translocation as compared to a healthy control.

In some preferred embodiments, the mutation analysis is conducted for point mutations and therefore, this method has a technical advantage over other methods in which a karyotyping procedure is used because karyotyping is unlikely to detect point mutations. Thus, the present method provides an advantage for diagnosing patients whose karyotypes do not show apparent abnormalities, but whose disease is associated with point mutations.

In some embodiments, at least one of the following MDS-associated genes is analyzed for a point mutation: ASXL1, ETV6, EZH2, IDH1, IDH2, NRAS, CBL, RUNX1, SF3B1, SRSF2, TET2, TP53, U2AF1, and ZRSR2. These genes are identified by their gene bank accession numbers and description in Table 1 below.

TABLE 1

MDS-Associated Genes

| Gene | Accession | Definition |
|---|---|---|
| ASXL1 | NM_015338 | *Homo sapiens* additional sex combs like transcriptional regulator 1 (ASXL1), transcript variant 1, mRNA |
| ETV6 | NM_001987 | *Homo sapiens* ets variant 6 (ETV6), mRNA |
| EZH2 | NM_152998 | *Homo sapiens* enhancer of zeste homo log 2 (*Drosophila*) (EZH2), transcript variant 2, mRNA |
| GNAS | NM_000516 | *Homo sapiens* GNAS complex locus (GNAS), transcript variant 1, mRNA |
| IDH1 | NM_005896 | *Homo sapiens* isocitrate dehydrogenase 1 (NADP+), soluble (IDH1), transcript variant 1, mRNA |
| IDH2 | NM_002168 | *Homo sapiens* isocitrate dehydrogenase 2 (NADP+), mitochondrial (IDH2), transcript variant 1, mRNA |
| NRAS | NM_002524 | *Homo sapiens* neuroblastoma RAS viral (v-ras) oncogene homolog (NRAS), mRNA |
| CBL | NM_05188 | *Homo sapiens* Cbl proto-oncogene, E3 ubiquitin protein ligase (CBL), mRNA |
| PTPN11 | NM_080601 | *Homo sapiens* protein tyrosine phosphatase, non-receptor type 11 (PTPN11), transcript variant 2, mRNA. |
| RUNX1 | NM_001754 | *Homo sapiens* runt-related transcription factor 1 (RUNX1), transcript variant 1, mRNA |
| SF3B1 | NM_012433 | *Homo sapiens* splicing factor 3b, subunit 1, 155 kDa (SF3B1), transcript variant 1, mRNA |
| SRSF2 | NM_001195427 | *Homo sapiens* serine/arginine-rich splicing factor 2 (SRSF2), transcript variant 2, mRNA |
| TET2 | NM_001127208 | *Homo sapiens* tet methylcytosine dioxygenase 2 (TET2), transcript variant 1, mRNA |
| TP53 | NM_001126113 | *Homo sapiens* tumor protein p53 (TP53), transcript variant 4, mRNA |
| U2AF1 | NM_1025203 | *Homo sapiens* U2 small nuclear RNA auxiliary factor 1 (U2AF1), transcript variant b, mRNA |
| ZRSR2 | NM_005089 | *Homo sapiens* zinc finger (CCCH type), RNA-binding motif and serine/arginine rich 2 (ZRSR2), mRNA |

In further embodiments, at least two or more of the following MDS-associated genes are analyzed for a point mutation: ASXL1, ETV6, EZH2, IDH1, IDH2, NRAS, CBL, RUNX1, SF3B1, SRSF2, TET2, TP53, U2AF1, and ZRSR2. In further embodiments, a set the following MDS-associated genes is analyzed for a point mutation: ASXL1, ETV6, EZH2, IDH1, IDH2, NRAS, CBL, RUNX1, SF3B1, SRSF2, TET2, TP53, U2AF1, and ZRSR2. In some embodiments, the set of the MDS-associated genes is analyzed in combination with other genes and/or other abnormalities indicative of MDS, such as cytopenia, low hemoglobin, fatigue and/or fever.

Each of the MDS-associated genes in Table 1 is included on the TruSight™ Myeloid Sequencing Panel available from Illumina®. Additional information regarding the MDS-associated genes of Table 1, including sequence listings, is publicly available from the National Center for Biotechnology Information (NCBI).

The MDS-associated genes of Table 1 were selected from the 54 target genes in the Myeloid Sequencing Panel. Persons of skill in the art will recognize that additional genes or a different combination of genes may be selected. Persons of skill in the art will also know that similar panels are available from a number of other suppliers including Agilent Technologies (ClearSeq AML), Integrated DNA Technologies (xGen® AML Cancer Panel), ARUP Laboratories, Life Technologies, and others.

Various methods are suitable for detecting a mutation in MSD-associated genes. In some particularly preferred embodiments, a suitable method is selected from non-Sanger-based high-throughput DNA sequencing technologies, abbreviated as next-generation sequencing (NGS). In one embodiment of the NGS mutation analysis, an input DNA sample is cleaved into short sections and annealed to a slide using adaptors. A PCR reaction is carried out to amplify the number of DNA copies. The slide is then reacted with fluorescently labeled nucleotides, terminators and DNA polymerase. One cycle of polymerization is completed and an image is taken of the slide. The slide is then prepared for the next cycle by removing terminators and the next base is then added in a DNA polymerization process. The process is repeated, adding one nucleotide in each cycle and recording an image after each cycle. A computer is then used to process the captured images and generate a DNA sequence.

A person of skill will appreciate that many other modifications of the NGS analysis can be performed. It will be further appreciated that the term "NGS-analysis" is understood broadly and includes any DNA sequencing method which is performed by adhering a DNA sample to a solid substrate and without separating DNA molecules according to their length by electrophoretic gel. At least in some embodiments, the NGS analysis can be performed with at least one of the following kits: ILLUMINA (SOLEXA) SEQUENCING™ Kit available from Illumina, Inc., ROCHE 454 SEQUENCING™ available from Roche, Inc., ION TORRENT: PROTON/PGM SEQUENCING™ available from Thermofisher, Inc., and SOLID SEQUENCING™ available from Thermofisher, Inc.

Additional description of NGS protocols can be found in R. Luthra, et al., "Next-generation sequencing-based multi-gene mutational screening for acute myeloid leukemia using MiSeq: applicability for diagnostics and disease monitoring", *Haematologica*, 2014; 99(3): 465-473; and M. Fernandez-Mercado, et al., "Targeted re-sequencing analysis of 25 genes commonly mutated in myeloid disorders in del(5q) myelodysplastic syndromes", *Haematologica*, 2013; 98(12): 1856-1864. A detailed review of NGS is provided in A. Mori, et al., "Next generation sequencing: new tools in immunology and hematology", *Blood Res., December* 2013; 48(4): 242-249.

Various samples from a patient can be used for performing a mutation analysis of MDS-associated genes. Such samples may include cells from peripheral blood plasma and cell-free DNA (abbreviated as cf-DNA) obtained from peripheral blood plasma or serum. In some preferred embodiments, a point mutation analysis of MDS-associated genes is performed with cell-free DNA obtained from peripheral blood plasma or serum. Thus, the present method provides a significant technical advantage of providing diagnostics, treatment, management and monitoring to a patient with cytopenia because the method has a high sensitivity and does not require obtaining a bone marrow sample.

Figure 1:
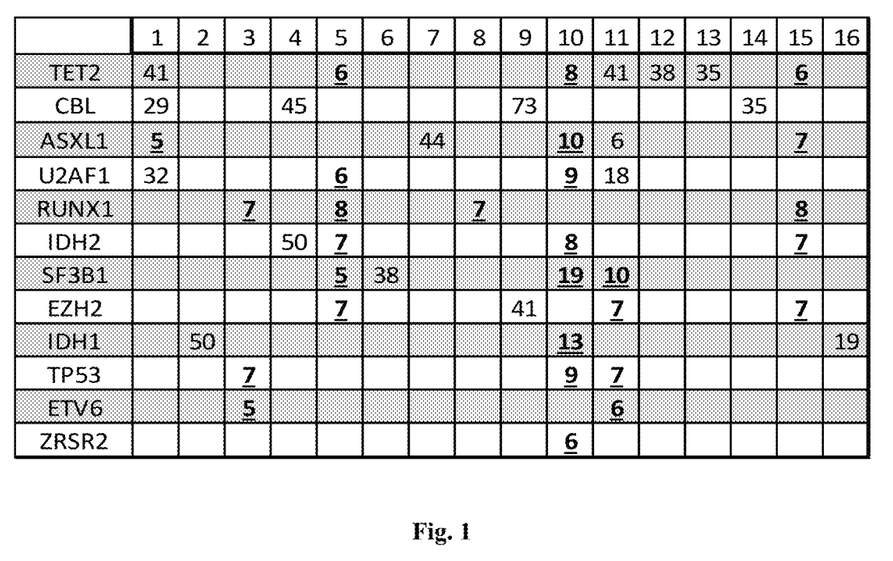
FIG. 1 is a mutation analysis of MDS-associated genes in patients. The analyzed genes are listed in the left column. Each patient is identified by a number from 1 to 16 in the first row. Point mutations identified by both the Sanger sequencing method and NGS analysis are shown in black. Point mutations identified by the NGS analysis, but missed in the Sanger sequencing method are in bold and underlined.

As shown in FIG. 1, it has been unexpectedly discovered that the NGS mutation analysis of MDS-associated genes on cell-free DNA obtained from peripheral blood plasma or serum is a more accurate and sensitive method for identifying patients in need of MDS treatment. MDS-associated genes analyzed are shown in the left column of FIG. 1 and include the MDS-genes listed in Table 1.

FIG. 1 reports results of the NGS mutation analysis for 16 patients, each of the patients identified with numbers 1 through 16 in the first row of the table in FIG. 1. Both NGS sequencing and Sanger sequencing was performed for NRAS exon 3, TET2 exons 4, and 13-16, EZH2 exons 10 and 11, and TP53 exon 4. Amplicons were confirmed for each sample by running on agarose gel. Samples were pooled and a data sheet was generated using Illumina® Experiment Manager. MiSeg™ Reporter was used for analysis and Variant Studio was used for calling. For confirmation of variant calling NextGene (SoftGenetics, State College, Pa.) software was used. Average sequencing coverage (X) across the entire coding regions was 4000 of 94% of the sequenced amplicons. This allows to reliably detect a mutation if present in 3% of DNA.

The NGS-sequencing of cell-free DNA in peripheral blood plasma from the 16 patients with early stage MDS showed at least one or more mutated gene confirming the diagnosis of MDS. Cell-free DNA in peripheral blood plasma from normal controls showed no evidence of mutations. Additional mutations were detected in 8 (50%) samples that were not detected when Sanger sequencing was used analyzing DNA extracted from whole blood (FIG. 1). These additional mutations are shown in bold underlined numbers, while mutations that were detected by both Sanger and NGS-sequencing are shown in regular font. The numbers represent mutant allele frequency in DNA sample in percent. As can be seen from FIG. 1, the mutant allele frequency in patient 1 for gene ASXL1 is 5 percent.

Of the 16 patients, 5 (31%) showed no abnormalities in the whole blood DNA at all. These samples would likely to be falsely identified as normal if Sanger sequencing had been performed on whole blood. Mutations detected in peripheral blood plasma by the NGS mutation analysis were at frequency<15%, which is in general below the detection level of Sanger sequencing even if they are present at the same frequency in the whole blood DNA. However, most likely the level or frequency of the mutant DNA in the whole blood DNA is significantly lower as confirmed in the samples that were tested by the NGS mutation analysis.

Figure 2:
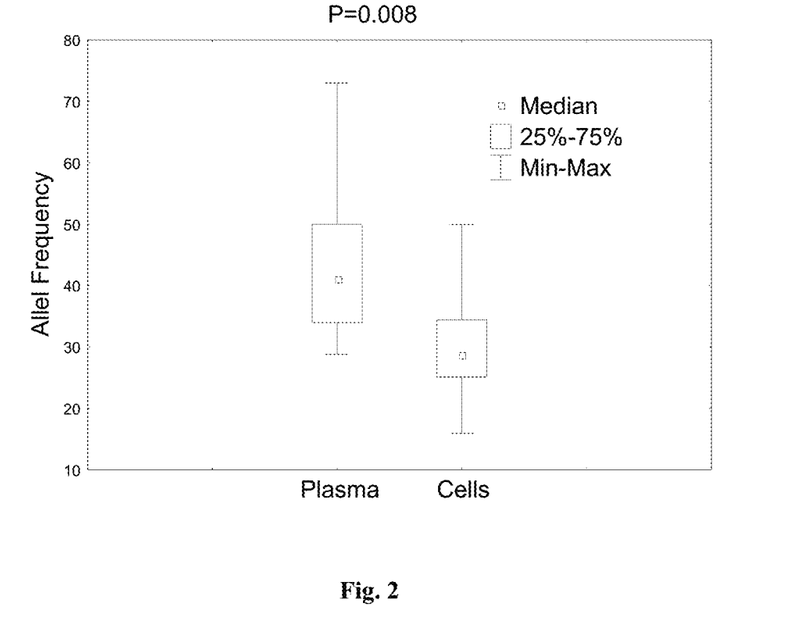
FIG. 2 is a plot comparing allelic frequency for cell-free DNA samples from peripheral blood plasma and cell-based DNA samples from peripheral blood plasma.

As further shown in FIG. 2, it was also unexpectedly discovered that conducting a mutation analysis on peripheral blood plasma cell-free DNA is a much more sensitive method in comparison to conducting a mutation analysis on DNA from whole peripheral blood.

As shown in FIG. 2, the NGS mutation analysis was performed on 5 DNA samples extracted from whole peripheral blood. Four of the five samples showed results identical to those detected from the peripheral blood plasma cell-free DNA. However, one sample showed a mutation in RUNX1 at 7% that is detected in the cell-free peripheral blood plasma DNA and not in the whole blood DNA by NGS.

More importantly, the frequency of the detected mutations, allele frequency in blood plasma as detected by the NGS analysis was significantly (P=0.008) higher in cell-free DNA from peripheral blood plasma, suggesting higher sensitivity and enrichment of plasma by neoplastic DNA (FIG. 2).

In one embodiment, the invention provides a method for managing a patient with MDS, comprising a screening test for MDS which is a less complicated, minimally-invasive and has an increased sensitivity. The time needed to perform the test is also reduced in comparison to conventional tests.

In further embodiments, the invention provides a method for monitoring a patient with MDS, comprising a screening test for MDS which is a less complicated, minimally-invasive and has an increased sensitivity. The time needed to perform the test is also reduced in comparison to conventional tests. The term "monitoring" is to be understood broadly and includes conducting a test concurrently with or after completion of treatment to determine the status of patient's disease. A monitoring method permits a doctor to determine whether a treatment protocol is working and whether additional or different treatment may be needed.

Further embodiments allow more rapid identification and initiation of an appropriate treatment protocol to provide supportive care to relieve symptoms, slow progression of the disease, and/or potentially cure the disease.

Known treatments that can be administered to a patient diagnosed by the NGS mutation analysis include transfusion therapy, erythropoiesis-stimulating agents, antibiotics, drug therapy, chemotherapy with or without stem cell therapy, entry into clinical trials, or combinations thereof. (A. M. Zeidan, et al., "Current therapy of myelodysplastic syndromes", *Blood Rev.* 2013 September; 27(5): 243-259).

The inventive method facilitates accurate and more frequent monitoring of patient's progress during treatment, and/or modification of treatment, without requiring the patient to undergo additional bone marrow aspiration procedures. Follow-up testing after completion of treatment is also greatly improved by the inventive method.

The NGS analysis of cell-free DNA in peripheral blood plasma or serum using a number of MDS-associated genes, presents an objective test for identifying or confirming patients as patients with MDS. It has been discovered that peripheral blood plasma is enriched with tumor-specific DNA in patients with MDS. Furthermore, a mutation analysis of cell-free DNA in blood plasma can detect subclones with mutations and can predict the emergence of new clones. The analysis of cell-free DNA in peripheral blood plasma using NGS provides important data on tumor load, which can be used to monitor therapy, and predict progression, and also reduces the need for performing bone marrow biopsies.

Prior to the present method based on the mutation analysis of cell-fee DNA from peripheral blood plasma or serum, detection of molecular abnormality in a patient with suspected MDS was difficult to accomplish without performing a bone marrow biopsy. When the blast count in bone marrow is within normal limits, diagnosis is subjective without the demonstration of molecular abnormality by cytogenetic or molecular studies.

Due to the cytopenia in peripheral blood, detecting molecular abnormalities in peripheral blood cells can be difficult, especially in early disease even when highly sensitive method is used. Evaluation of the inventive method shows that even when the NGS mutation analysis is used, it is possible to miss the detection of mutations in peripheral blood cells. In contrast, using cell-free DNA from peripheral blood plasma in the NGS mutation analysis detects mutations more reliably.

Peripheral blood plasma or serum is easily accessible and the potential of using it for diagnosing or confirming MDS can reduce the need for bone marrow biopsies significantly.

While not wishing to be bound by theory, the fact that peripheral blood plasma is enriched with neoplastic DNA is believed to be due to the relatively high apoptosis of neoplastic cells in MDS. These neoplastic cells die in bone marrow and release their DNA in circulation. Most likely this DNA is in the form of apoptotic bodies, microvessels, or protein-DNA complex.

Demonstration of molecular abnormality in a patient with symptoms which could be indicative of MDS is very important for confirmation of diagnosis, prognosis, and choosing a therapeutic approach. This is particularly important in regard to patients with early MDS (blasts in bone marrow <5%). In this group of patients, frequently the diagnosis remains speculative even after performing bone marrow aspiration and biopsy. Morphologic changes can be subtle and cytogenetic abnormalities may not be present.

With recent advances in molecular characterization of MDS, the diagnosis of MDS is becoming more reliant on molecular testing in detecting the presence of an abnormal clone. Furthermore, the type of the detected molecular abnormality may provide significant information for predicting prognosis and determining clinical course and therapy.

On the other hand, cytopenia, which is the major presenting symptom for suspecting MDS diagnosis, can be seen in several reactive processes and represents a diagnostic dilemma in determining whether bone marrow biopsy is needed or not.

Performing a molecular analysis by using peripheral blood cells is a possible approach to confirm the presence of MDS. However, due to the cytopenia in peripheral blood, detecting molecular abnormalities in peripheral blood cells requires high sensitivity testing and the NGS mutation analysis provides significantly better sensitivity than Sanger sequencing. Negative results do not always rule out the presence of MDS.

In samples obtained with consent from MDS patients with blast counts less than 5%, the present NGS mutation analysis detects abnormalities in all cases supporting the conclusion that that the present NGS mutation analysis is a highly accurate and sensitive method for identifying patients as MDS patients even at the earlier stages of the disease.

The NGS mutation analysis when performed using cell-free DNA is more accurate and sensitive in comparison to Sanger sequencing of peripheral blood cellular DNA. It has been also determined that the NGS mutation analysis with blood plasma cell-free DNA is more accurate and sensitive in detecting molecular abnormalities and confirming MDS diagnosis in comparison to the NGS mutation analysis performed on cellular DNA. It has been also unexpectedly found that the cell-free DNA is less diluted by normal cell DNA and more enriched by MDS-specific DNA. This finding is supported by the significantly higher mutant allele detected in cell-free DNA as compared with cellular DNA using the NGS mutation analysis (P=0.008), as shown in FIG. 2.

Previous studies (Ma et al, 2009; Yeh et al, 2009; Ma et al, 2008; Ma et al, 2007; Rogers et al, 2004; Ahmed et al, 2003; Jilani et al, 2003) show that patients with more advanced MDS have more circulating cell-free DNA, thus the detection of molecular abnormalities to confirm the diagnosis of MDS should be easier in these cases.

It has been determined that cell-free DNA is more reliable than peripheral blood cellular DNA in detecting molecular abnormalities in patients with MDS even when the blast count is less than 5%. Furthermore, the NGS mutation analysis is more accurate than Sanger sequencing and should be considered as the method of choice for analyzing cell-free DNA in identifying patients as MDS patients and administering a treatment for MDS.

Example 1. Patients and Samples

Peripheral blood (PB) samples were collected from 16 patients confirmed to have MDS by bone marrow evaluation and from four age-matched normal controls. All patients had blasts <5%.

Cell-free DNA from peripheral blood plasma and cellular DNA from PB cells was extracted. The characteristics of the patients are listed in Table 2.

TABLE 2

Patient Population

|  |  | Number |
|---|---|---|
| Cytogenetics | Diploid | 13 |
|  | del (6)(q21) | 1 |
|  | Trisomy 8 | 1 |
|  | Complex | 1 |
| Gender | Female | 7 |
|  | Male | 9 |

|  | Median | Range |
|---|---|---|
| WBC | 3.5 | 2.0-16.4 |
| HGB | 10.5 | 9.6-12.6 |
| MCV | 102.8 | 91-106 |
| Platelets | 103 | 74-194 |
| % Lymph | 26.9 | 14.3-52.4 |
| % Monocytes | 9.1 | 6.3-19.9 |
| % Polys | 59.7 | 37-77 |
| Age | 73 | 53-92 |

Example 2. DNA Isolation

Total nucleic acid was isolated from plasma using a NucliSens extraction kit (BioMerieux Inc., Durham, N.C.) according to the manufacturer's instructions. DNA from PB cells was isolated using a QIAamp DNA Blood Mini Kit (Qiagen, Valencia, Calif.) according to the manufacturer's instructions.

Example 3. Genes Sequencing

Using Sanger sequencing and NGS, mutations were analyzed in the following genes: ASXL1, ETV6, EZH2, IDH1, IDH2, NRAS, CBL, RUNX1, SF3B1, SRSF2, TET2, TP53, U2AF1, and ZRSR2. Sanger sequencing was performed using a standard protocol. The primer pairs were designed to encompass >90% of reported mutations in these genes. Polymerase chain reaction (PCR) products were purified and sequenced in both forward and reverse directions using an ABI PRISM 3730XL Genetic Analyzer (Applied Biosystems, Foster City, Calif.). Sequencing data were base-called using sequencing analysis software and assembled and analyzed with SeqScape software (Applied Biosystems).

NGS was performed using the Illumina MiSeq system (San Diego, Calif.); NGS, amplification, and indexing were performed as recommended by the manufacturer. Amplicons were confirmed for each sample by running an agarose gel. Samples were pooled and the experiment sheet was generated using Illumina Experiment Manager. MiSeq Reporter was used for analysis and Variant Studio was used for calling. For confirmation of variant calling, NextGene software (SoftGenetics, State College, Pa.) was used. Average sequencing coverage across the entire coding regions was 4,000 in 94% of the sequenced amplicons. This reliably allowed detection of mutations if present in at least 3% of mutant DNA.

Example 4. Confirming the Presence of Neoplastic Abnormal MDS Clone Using Cell-Free DNA The 16 patients were confirmed to have MDS through examination of bone marrow samples and complete cytogenetic and molecular evaluation. The characteristics of the patients are listed in Table 2.

One of the 16 patients had chronic myelomonocytic leukemia (CMML) and the rest had refractory anemia. Nine patients (56%) were males. All 16 patients had refractory anemia, two with ring sideroblasts. Cytogenetic data of bone marrow showed one patient with a complex abnormality, one with trisomy 8, and one with deletion in the long arm of chromosome 6. Upon the NDS mutation analysis of blood plasma cell-free DNA, all 16 patients showed at least one mutated gene, confirming the presence of an abnormal clone consistent with MDS. No abnormality was detected in any of the four samples from normal control individuals.

Eight patients (50%) showed mutation in one gene and the remaining eight patients (50%) showed mutations in two or more genes (FIG. 1).

Example 5. NGS of Cell-Free DNA is More Sensitive than Sanger Sequencing of Peripheral Blood Cellular DNA Five of the 16 patients (31%) had mutations detected by NGS of cell-free DNA while Sanger sequencing of peripheral blood cellular DNA showed no evidence of mutation. These patients would have been considered negative for MDS if Sanger sequencing of cellular DNA had been used. Of the remaining 11 patients, 3 (27%) showed additional mutations that were not detected by Sanger sequencing. Overall, 8 of the 16 patients (50%) showed mutations in plasma cell-free DNA by NGS that were not detected in whole blood DNA by Sanger sequencing.

All mutations detected in cell-free DNA by NGS and not by Sanger sequencing in cellular DNA had allele frequency <20% (FIG. 1). This may explain the failure of detection by the Sanger sequencing. In general the detection level of Sanger sequencing is between 15 and 20%, while the NGS sequencing is approximately 5% (Chen et al, 2015).

Example 6. NGS is More Sensitive Using Cell-Free DNA as Compared with Using Cellular DNA Since the detection level of NGS is significantly better than that of Sanger sequencing, peripheral blood cellular DNA using NGS was tested and compared with the results obtained with cell-free DNA in five samples. Four of the five pairs (80%) showed identical results and one sample showed a mutation in RUNX1 at 7% in cell-free DNA that was not detected in DNA from cellular DNA.

Most likely this reflects the relative enrichment of plasma by tumor-specific DNA. To confirm this, the mutant allele frequency as detected in cell-free DNA was compared with that detected in peripheral blood cellular DNA. As shown in FIG. 2, the level of the mutant allele in the cell-free DNA is significantly higher than that in the cellular DNA from peripheral blood cells (P=0.008). This suggests higher sensitivity and enrichment of neoplastic DNA in blood plasma (FIG. 2).

What is claimed is:

1. A method for treating a patient suspected of having a hematologic malignancy, the method comprising:
    (a) testing the patient by:
        obtaining a sample of peripheral blood plasma or serum from the patient;
        extracting cell-free DNA from the sample;
        performing a mutation analysis on a panel of MDS-associated genes in the cell-free DNA, wherein the panel of MDS-associated genes comprises ASXL1, ETV6, EZH2, IDH1, IDH2, NRAS, CBL, RUNX1, SF3B1, SRSF2, TET2, TP53, U2AF1, and ZRSR2, wherein the mutation analysis comprises next-generation sequencing (NGS);
    (b) detecting one or more mutations in the panel of genes;
    (c) diagnosing the patient as having a hematological malignancy; and
    (d) administering to the patient a treatment selected from a growth factor, blood transfusion, desferoxamine, erythropoietin, a chemotherapeutic agent, stem cell transplant, and any combination thereof.

2. The method of claim 1, wherein the patient has an increase in bone marrow blasts of less than 5% in comparison to a healthy control.

3. The method of claim 1, wherein the patient has no apparent karyotypic abnormalities.

4. The method of claim 1, wherein the patient manifests cytopenia.

5. The method of claim 1, wherein the mutation analysis is performed without performing bone marrow biopsy.

6. The method of claim 1, wherein the hematologic malignancy is myelodysplastic syndrome (MDS).

7. A method for treating myelodysplastic syndrome (MDS), the method comprising:
    (a) testing a patient by:
        selecting the patient from a group of patients presenting with cytopenia;
        obtaining a sample of the patient's blood plasma or serum;
        extracting cell-free DNA from the sample;
        performing a mutation analysis on a panel of MDS-associated genes in the cell-free DNA, wherein the panel of MDS-associated genes comprises ASXL1, ETV6, EZH2, IDH1, IDH2, NRAS, CBL, RUNX1, SF3B1, SRSF2, TET2, TP53, U2AF1, and ZRSR2;
    (b) detecting one or more mutations in the panel of genes; and
    (c) administering a treatment to the patient selected from a growth factor, blood transfusion, desferoxamine, erythropoietin, a chemotherapeutic agent, stem cell transplant, and any combination thereof.

8. The method of claim 7, wherein the mutation analysis is repeated periodically to monitor the patient's progress.

9. The method of claim 7, wherein the mutation analysis comprises performing a procedure selected from the group consisting of NGS, PCR, hybrid capture and any combination thereof.

10. The method of claim 9 wherein the mutation analysis further comprises karyotyping and/or blood analysis.

11. The method of claim 7, wherein the step of obtaining a cell-free DNA sample from the patient's peripheral blood plasma and the step of conducting the mutation analysis on the cell-free DNA sample for the MDS-associated genes are repeated after the treatment has begun, and wherein the treatment is modified if additional mutations in the MDS-associated genes are detected.

12. A method for treating a hematologic malignancy in a patient, the method comprising:
    (a) testing the patient by:
        extracting a peripheral blood plasma sample or serum of from the patient;
        extracting cell-free DNA from the sample;
        performing mutation analysis on a panel of MDS-associated genes using next generation sequencing, wherein the panel of MDS-associated genes comprises ASXL1, ETV6, EZH2, IDH1, IDH2, NRAS, CBL, RUNX1, SF3B1, SRSF2, TET2, TP53, U2AF1, and ZRSR2;
    (b) detecting one or more mutations in the panel of genes; and
    (c) administering a treatment to the patient selected from a growth factor, blood transfusion, desferoxamine, erythropoietin, a chemotherapeutic agent, stem cell transplant, and any combination thereof.

* * * * *

UNITED STATES PATENT AND TRADEMARK OFFICE
CERTIFICATE OF CORRECTION

PATENT NO. : 10,604,801 B2
APPLICATION NO. : 14/937937
DATED : March 31, 2020
INVENTOR(S) : Maher Albitar

Page 1 of 1

It is certified that error appears in the above-identified patent and that said Letters Patent is hereby corrected as shown below:

On the Title Page

Item [54], and in the Specification, Column 1, Line 1 "SEQUECING" should read --SEQUENCING--

Signed and Sealed this
Fifth Day of May, 2020

Andrei Iancu
*Director of the United States Patent and Trademark Office*